United States Patent [19]

Homm et al.

[11] 4,043,338

[45] Aug. 23, 1977

[54] PHARMACEUTICAL FORMULATION APPLICATOR DEVICE

[75] Inventors: Roger Homm, Neshanic; Gilbert Katz, Boonton, both of N.J.

[73] Assignee: Ortho Pharmaceutical Corporation, Raritan, N.J.

[21] Appl. No.: 715,791

[22] Filed: Aug. 19, 1976

Related U.S. Application Data

[63] Continuation of Ser. No. 355,366, April 30, 1973, abandoned.

[51] Int. Cl.$^2$ .............................................. A61M 31/00
[52] U.S. Cl. ................................... 128/260; 128/243; 128/303.11
[58] Field of Search .................... 128/243, 260, 303.11

[56] References Cited

U.S. PATENT DOCUMENTS

| 88,695 | 4/1869 | Davidson | 128/243 |
|---|---|---|---|
| 365,969 | 7/1877 | Collins | 128/243 |

Primary Examiner—Aldrich F. Medbery
Attorney, Agent, or Firm—Benjamin F. Lambert

[57] ABSTRACT

A device for introducing pharmaceutical formulations into a body orifice is described. The device consists of a hollow tube constructed of a rigid but flexible material which is closed at at least one end. A freely sliding, rigid tube or rod is contained within the hollow tube and is attached to one end of it. The outer tube is slit longitudinally near the end where the two tubes are joined to form a plurality or uniform distensible ribs which distend or flex when pressure is applied to the end to which the inner tube is attached.

1 Claim, 7 Drawing Figures

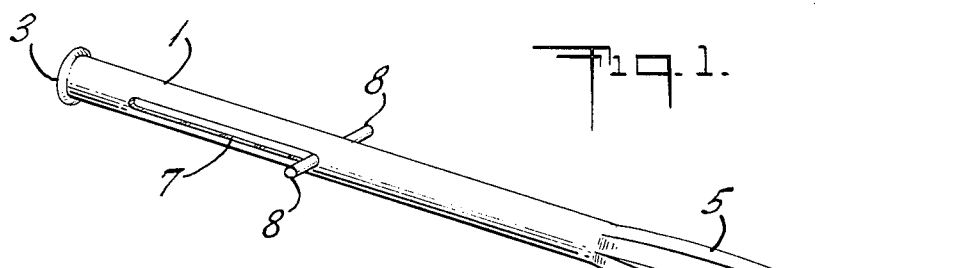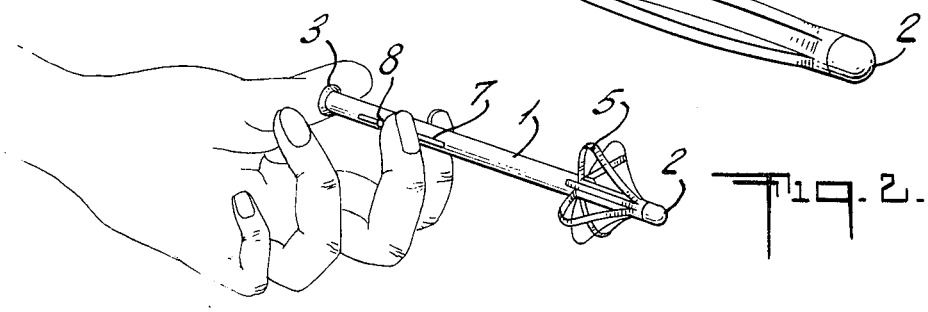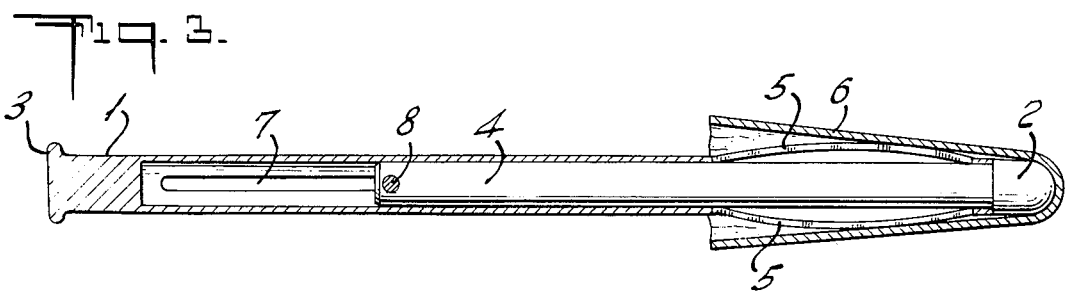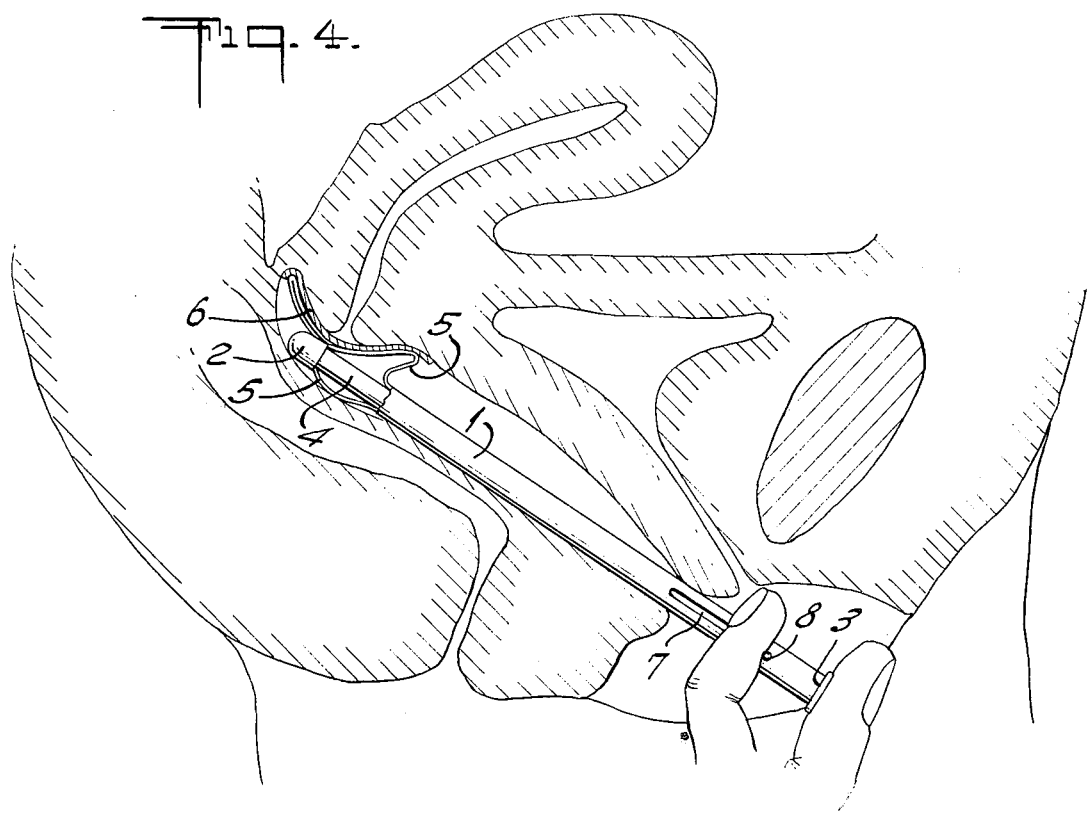

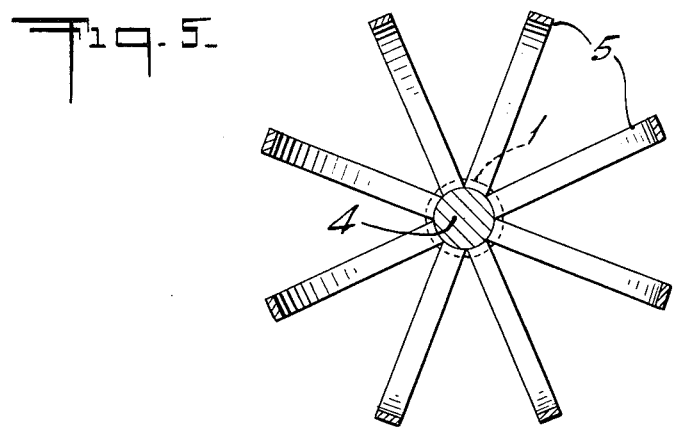
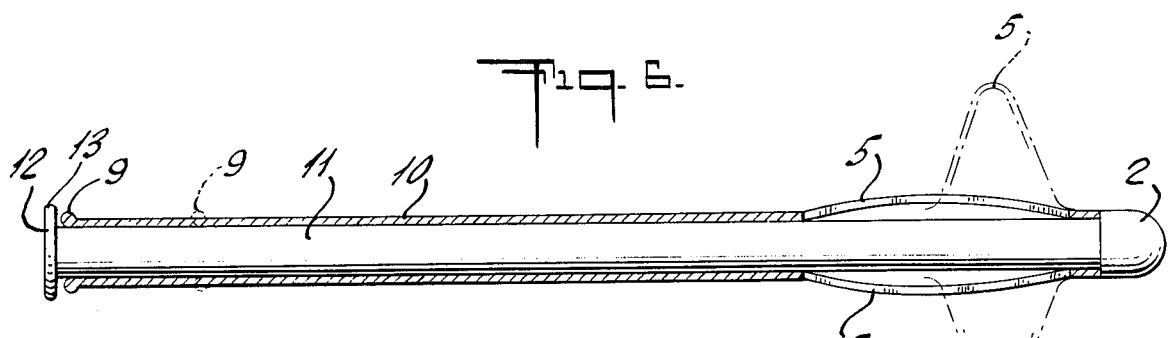
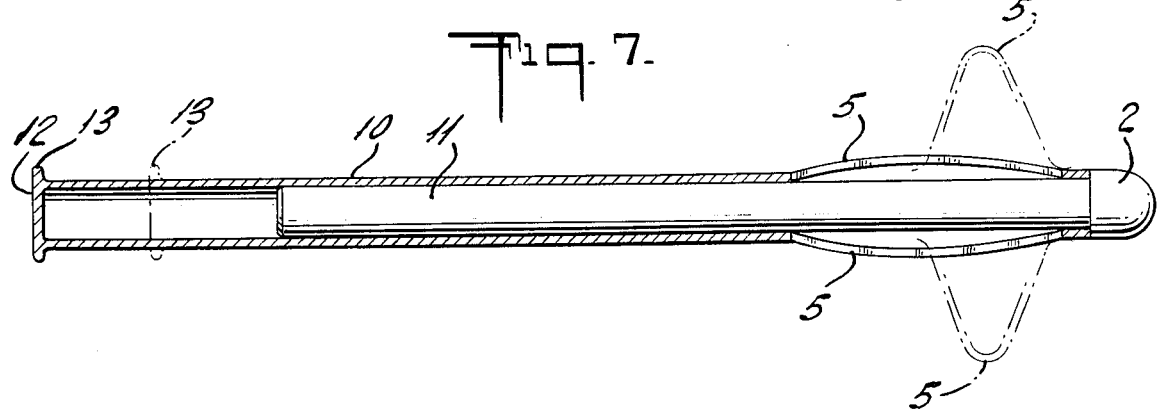

PHARMACEUTICAL FORMULATION APPLICATOR DEVICE

This is a continuation of application Ser. No. 355,366 filed Apr. 30, 1973 and now abandoned.

The present invention relates to new and useful improvements in dispensers for pharmaceutical formulations and in particular to dispensers adapted to the application of pharmaceutical formulations onto the interior surface of body orifices such as the vaginal cavity.

It is often desirable to introduce matter into body cavities such as the vagina for the treatment of vaginal infections or for contraceptive purposes. Many devices have been developed to effect such introduction but each of them suffers from one or more disadvantages. It has been the practice to introduce viscous liquid or jelly-like pharmaceutical formulations into the vagina by means of an applicator filled with a pharmaceutical formulation from a large supply-storage tube. Besides being mechanically awkward, such applicators are ineffective for the introduction of fibrous materials such as woven an nonwovenpads, membranes, foam sheets and the like into the vagina. In addition, applicators of the type currently used in the art are generally unsuited for spreading the pharmaceutical formulation onto the interior surface of the vagina. When the prior art applicators are employed, the material is generally deposited in the vaginal cavity in a single rounded mass. When so deposited, the mass is unable to spread over the entire surface of the vagina and, hence, will be less effective for the intended purpose.

By means of the present invention, an applicator for pharmaceutical formulations is provided by which formulations in the nature of fibrous materials as well as foams and jellies can be introduced into the vagina and applied to its interior surfaces.

The invention will be more clearly understood by reference to the application and drawings in which:

FIG. 1 is a perspective view of one embodiment of the device in the relaxed state;

FIG. 2 is a perspective view of the device in the flexed state;

FIG. 3 is a cross section of the device in the semi-flexed state and containing a membrane in position over the partially distended ribs;

FIG. 4 is a cross section of the device positioned in the vaginal cavity;

FIG. 5 is a front perspective view looking down the length of the device and showing the ribs in a distended position.

FIG. 6 is a cross section of a second embodiment of the invention.

FIG. 7 is a cross section of a second embodiment of the invention in the flexed state;

In the preferred embodiment, the applicator device consists of a hollow tube, 1, constructed of a rigid but flexible material, such as molded plastic, spirally wound paper and the like, which is closed at both ends, 2 and 3. Although both ends are shown as closed in the drawings, only the end to which the inner tube is attached need be closed. It is preferred that the insertion end, 2, of the tube, 1, be rounded. Contained within the tube is a second, freely-sliding, rigid tube, 4, one end of which is attached to the rounded end, 2. The tube, 1, is longitudinally slit near the rounded end, 2, to form a plurality of uniform distensible ribs, 5. In the preferred embodiment, the free end of the inner tube, 4, and the upper end of the outer tube, 1, are provided with at least two opposed slots, 7, adapted to receive finger actuating means comprising one or more finger support means, 8. Flexation of the ribs is achieved by pushing on the thumb actuating means located on the distal end, 3, of the tube, 1, while simultaneously pulling up on the finger supports, 8. Operation of the device by means of the finger supports is shown in FIG. 2. The finger supports, 8, are not essential to the device, however; the ribs can also be distended by pressing the rounded end, 2, against any object which offers some resistance.

In utilizing the invention, the pharmaceutical formulation is placed on the ribbed end of the applicator while the device is in the unflexed state. In the case of foams or jellies, etc., the ribs can be coated with the desired formulation; because of the inherent difficulties involved when foams or jellies are employed it is sometimes difficult to administer accurate doses with such formulations. In the case of fibrous materials, the material is wrapped around the ribbed end and the device is alternately flexed and relaxed so as to catch the material between the ribs and thus hold it in place. In FIG. 3, a membrane is shown wrapped around the ribs, 5, of the device in the relaxed state. The device is then inserted into the vagina while in the relaxed state; the ribs are distended either by pressing the rounded end against the cervix or by pulling up on the finger supports. The formulation is thereby applied to the interior walls of the vagina. The device is then returned to its relaxed state so that it can be withdrawn from the vagina.

A second embodiment of the invention is illustrated in FIG. 6. In this embodiment, the flat end, 9, of the outer tube, 10, is open, and the inner rod, 11, projects beyond the tip of the free end of the outer tube. In this embodiment, flection is achieved by gripping the outer tube with one hand while pulling on the tip of the inner rod with the other hand. When the device is in its relaxed state, the tip, 12, abuts the flat end, 9, of the outer tube. The unattached end, 12, of the rod 11 and the open end 9 of the tube 10 alternatively may be provided with collars 13 and 9 respectively, to facilitate handling of the tubes.

We claim:

1. A device for dispensing a pharmaceutical formulation into body cavities which comprises:
a tube having a plurality of lengthwise, elongated ribs at one end, said tube being disposed to incorporate said formulation on said ribs;
a cylindrical rod slidably positioned within said tube and connected to said tube at the end containing said elongated ribs, the distal end of said tube being essentially flat is shape and comprising thumb actuating means, the free end of said rod and the distal end of said tube containing two opposed slots for the receipt of finger actuating means comprising at least one moveable finger support means, said cylindrical rod being disposed in pressure responsive relation to said tube such that pressure applied between the thumb actuating means and said finger acutating means causes the elongated ribs to distend, thereby depositing the pharmaceutical formulation on the interior walls of the cavity.

* * * * *

UNITED STATES PATENT AND TRADEMARK OFFICE
CERTIFICATE OF CORRECTION

PATENT NO. : 4,043,338
DATED : Aug. 23, 1977
INVENTOR(S) : Roger Homm and Gilbert Katz It is certified that error appears in the above-identified patent and that said Letters Patent are hereby corrected as shown below:

In Column 1, line 54, "flexed state;" should read
---flexed state.---

In Column 2, line 54, "flat is shape" should read
in Claim 1            ---flat in shape---

Signed and Sealed this

Twenty-eighth Day of March 1978

[SEAL]

Attest:

RUTH C. MASON
Attesting Officer

LUTRELLE F. PARKER
Acting Commissioner of Patents and Trademarks